US008092840B2

(12) United States Patent  (10) Patent No.: US 8,092,840 B2
Luciano  (45) Date of Patent: Jan. 10, 2012

(54) DIETARY SUPPLEMENT AND A METHOD TO ENHANCE SLEEP AND LUCID DREAMING

(76) Inventor: Jeff Luciano, Ithaca, NY (US)

( * ) Notice: Subject to any disclaimer, the term of this patent is extended or adjusted under 35 U.S.C. 154(b) by 214 days.

(21) Appl. No.: 11/927,836

(22) Filed: Oct. 30, 2007

(65) Prior Publication Data

US 2008/0107754 A1 May 8, 2008

Related U.S. Application Data

(60) Provisional application No. 60/864,801, filed on Nov. 8, 2006.

(51) Int. Cl.
*A61K 31/045* (2006.01)
*A61K 31/197* (2006.01)
*A61K 31/40* (2006.01)
*A61K 31/4375* (2006.01)
*A61K 31/44* (2006.01)
*A61K 31/495* (2006.01)
*A61K 31/75* (2006.01)
*A61P 25/20* (2006.01)
*A61P 3/02* (2006.01)

(52) U.S. Cl. ........ 424/725; 424/641; 424/643; 424/729; 424/740; 514/52; 514/249; 514/251; 514/283; 514/345; 514/355; 514/356; 514/363; 514/415; 514/419; 514/474; 514/667; 514/727

(58) Field of Classification Search ........................ None
See application file for complete search history.

(56) References Cited

U.S. PATENT DOCUMENTS

2005/0244510 A1* 11/2005 Smith .......................... 424/617

OTHER PUBLICATIONS

Heinrich, Current Topics in Medicinal Chemistry (2003), vol. 3, p. 29-42.*
Darien Simon, M.S.—An Initiation into the world of Lucid Dreaming—Published by NAP & Associates, LLP, Ithaca, NY USA, (2006).

* cited by examiner

*Primary Examiner* — Johann Richter
*Assistant Examiner* — Frank Choi
(74) *Attorney, Agent, or Firm* — Brown & Michaels, PC

(57) ABSTRACT

A nutritional supplement for enhancing sleep and lucid dreaming in humans. It contains a combination of ingredients in proportions calculated to enhance lucid dreaming. The primary ingredients are *Calea ternifolia*, L-5-Hydroxytryptophan (L-5-HTP), and Vinpocetine. In addition, the nutritional supplement may include the secondary ingredient Melatonin and the tertiary ingredients Wild Lettuce Extract, Mugwort Extract, Dimethylaminoethanol Powder (DMAE), Passionflower Extract and Green Tea Extract. Further, various Vitamins may be added such as certain B vitamins, D and C, as well as Zinc, Magnesium and Calcium. The selection and amounts of the ingredients of the nutritional supplement promotes sleep and lucid dreaming in people who have taken the nutritional supplement prior to going to sleep.

12 Claims, No Drawings

US 8,092,840 B2

DIETARY SUPPLEMENT AND A METHOD TO ENHANCE SLEEP AND LUCID DREAMING

This application claims one or more inventions which were disclosed in Provisional Application No. 60/864,801, filed Nov. 8, 2006, entitled "DIETARY SUPPLEMENT TO ENHANCE LUCID DREAMING". The benefit under 35 USC §119(e) of the United States provisional application is hereby claimed, and the aforementioned application is hereby incorporated herein by reference.

FIELD OF THE INVENTION

The invention pertains to the field of dietary supplements. More particularly, the invention pertains to the use of a specific dietary supplement as a sleep aid and lucid dreaming enhancer in humans.

BACKGROUND OF THE INVENTION

Dreams have been recognized as sacred and spiritual experiences in many cultures around the world since the beginning of recorded history and perhaps even earlier. In the last century, the understanding of dreams has changed from one related exclusively to the spiritual to that pertaining to the physical/psychological realm. Toward the end of the twentieth century, the idea of lucid dreaming, or dreaming with deliberate intention and control, has moved from the world of shamans or spiritualists to realization that lucid dreaming can be achieved by anyone with the assistance of nutritional supplements and practice.

In order to facilitate the understanding of lucid dreaming, it is important to understand some basic elements about sleep and common, or non-lucid, dreaming. Humans have little understanding of why we sleep and dream. It is known, though, that the most vivid dreams occur during that phase of a sleep cycle called Rapid Eye Movement, or REM. It is known that healthy human adults go through about 3-6 cycles during a normal night's sleep, with each cycle being about 90-120 minutes long. REM sleep is usually the last phase of each cycle. Dreams can occur during any phase of any cycle, however, it is known that those dreams that occur during REM sleep tend to be the most vivid and visual and are usually not directly related to current events from the dreamer's experiences during the prior day.

As scientists began to learn more about the function of the human brain, it was discovered that the stimuli that produce images in dreams originate in a part of the brain not associated with thinking, desires or wishes, but a more primitive area. This lead to the neurophysiological or synthesis activation theory of dreams in which dreams result from random stimuli from the brain stem. In accordance with this theory, the cognitive parts of the brain play a minimal part in dreaming, probably limited to trying to make sense out of the random images originating from the primitive region of the brain stem.

It is surmised that dreaming is important in the development of memory. Human infants spend up to 16-18 hours a day sleeping and approximately 50% of this is in REM sleep. It has been determined that intense sessions of learning are followed by an increase in REM sleep. Dreaming also seems to play a role in emotional adjustment and in coping with traumatic experiences.

The term "Lucid Dreaming" was first used in 1913 by Fredrich van Eeden, a Dutch physician. Lucid dreaming is perhaps best defined as being aware that you are dreaming and is most likely to occur in REM sleep. Lucid dreaming can be either low level or high level. Low level lucid dreaming means that the dreamer is aware of being in a dream, but that not all the people, animals, things and scenes are constructs of his or her mind. In high level lucid dreaming, the dreamer is not only aware of being in a dream, but that all of the elements of the dream are being generated by their mind and are therefore potentially under their complete control.

According to studies done on lucid dreaming, these dreams may not only be potentially pleasurable or wish fulfilling, they can be tools for improving the quality of the dreamer's waking lives by facilitating healing, inspiring peak athletic performances, putting an end to recurrent nightmares, overcoming phobias, reducing or eliminating various anxieties and improving problem solving capabilities.

There are methods that have been developed by various researchers in the field, such as LaBerge and Rheingold. A common technique is used by the Lucidity Institute, founded by LaBerge, and is referred to as Mnemonic Induction of Lucid Dreams ("MILD"). The basics of the MILD technique involves various steps such as deliberately making yourself wake up during a dream cycle and immediately recalling the details of the dream. Over time, the dreamer is capable of recalling all of his or her dreams. The dreamer is then directed to use a "dream sign" to use as a cue to recognize that he or she is still dreaming. Becoming proficient at lucid dreaming requires a great deal of time, dedication and practice.

In order to enhance the training of a person to develop strong lucid dreaming skills, various devices have been devised. Such devices use light and/or sound to help trigger lucid dreams. Among the shamans of some primitive cultures, they would enhance their ability to have lucid dreams by using various drugs. However, as one can imagine, most of these substances are considered illegal in the U.S. Among the legal substances known to promote sleep (and possibly dreaming) are the B-vitamins, *Calea ternifolia*, melatonin, mugwort and passionflower. Before using such a substance alone or in combinations, it is important to know how to use it and what side effects it might cause. There is a need, therefore, for a safe but effective nutritional supplement that helps a person go to sleep and which can enhance lucid dreaming even without extensive mental preparation or exercises.

SUMMARY OF THE INVENTION

The present invention is a nutritional supplement that acts as a sleep aid and has been found to enhance lucid dreaming in humans. It consists of a combination of ingredients in proportions calculated to provide these results. The primary ingredients are *Calea ternifolia*, L-5-Hydroxytryptophan (L-5-HTP), and Vinpocetine. A secondary ingredient is Melatonin. In addition, the nutritional supplement of the invention may include Wild Lettuce Extract, Mugwort Extract, Dimethylaminoethanol Powder (DMAE), Passionflower Extract and Green Tea Extract. Further, various B-Vitamins, vitamin D, vitamin C, magnesium, calcium, as well as Zinc, may be added.

The relative amounts of these ingredients used in the nutritional supplement will be discussed in more detail in the Detailed Description of the Invention. The use of this nutritional supplement has been seen to assist a person in going to sleep as well as helping to promote lucid dreaming in people who take the supplement prior to going to sleep.

DETAILED DESCRIPTION OF THE INVENTION

The nutritional supplement of the invention is used as a sleep aid and a promoter of lucid dreaming in people who take it prior to going to sleep. To reiterate what was stated in the Background of the Invention, lucid dreaming is defined as being aware that the dreamer is dreaming. It is most likely to occur in REM sleep and can exist either at a low level or a high level. Low level lucid dreaming means that the dreamer is aware of being in a dream, but that not all the people, animals, things and scenes are constructs of his or her mind. In high level lucid dreaming, the dreamer is not only aware of being in a dream, but that all of the elements of the dream are being generated by their mind and are therefore potentially under their complete control.

The nutritional supplement of the invention is useful in promoting lucid dreaming in people who have not necessarily trained themselves to lucidly dream by performing extensive training techniques over a long period of time. It has been formulated to provide the best effect without the need to have undergone extensive mental conditioning, such as that taught by many organization and found in various publications, or subjecting oneself to some of the known mechanical devices invented by Laberge.

The primary ingredients are *Calea ternifolia* powder, L-5Hydroxytryptophan (L-5-HTP) and Vinpocetine. A secondary ingredient is Melatonin. Additional ingredients are Wild Lettuce Extract 4:1, Mugwort Extract 4:1, Dimethylaminoethanol Powder (DMAE), Passionflower Extract 10:1 and Green Tea Extract 10:1. Further, various vitamins may be added, such as B, C and D, as well as zinc, calcium and magnesium.

All of the ingredients of the nutritional supplement of the invention are known. For instance, *Calea ternifolia* is a known dream herb, used by the Chontal natives of Mexico. Green Tea is a well known drink that is high in antioxidants. Mugwort has been used for medicinal purposes for centuries and is known to cause a dreamy state of consciousness. Passionflower (*Passiflora incarnate*) has mild sedative properties that may be used to treat insomnia and anxiety. Wild Lettuce is an ingredient in some sleep tonics and has been historically regarded as a mild sedative. L-5-Hydroxytryptophan is known to raise serotonin levels which, in turn, improves sleep quality. Dimethylaminoethanol is thought to increase the levels of acetylcholine (a neurotransmitter) in the brain. Vinpocetine (*Vinca minor*) is known to aid memory and improve mental functioning. Melatonin is a natural hormone that regulates sleep in mammals. The B Vitamins are known to regulate the body's energy processes and promote good health. Vitamin C is also a necessary ingredient in maintaining good health. Zinc is used by the body in hundreds of enzymes which regulate many of the body's functions. Vitamin D, Calcium and Magnesium are additional elements that are utilized by the body.

Relative weights for the amounts of the main ingredients of the nutritional supplement are as follows:

| Weight Range | Ingredient |
|---|---|
| 300-600 mg | *Calea zacatechichi* powder |
| 30-70 mg | Wild Lettuce Extract 4:1 |
| 30-70 mg | Mugwort Extract 4:1 |
| 10-40 mg | L-5-HTP |
| 5-15 mg | DMAE |
| 14-30 mg | Passionflower Extract 10:1 |
| 5-15 mg | Green Tea Extract 10:1 |
| 1.0-4.0 mg | Vinpocetine |
| 300-600 mcg | Melatonin |

Additional ingredients, by weight:

| Range | Ingredient |
|---|---|
| 0.5-2.0 mg | Vitamin B-1 |
| 5-15 mg | Vitamin B-2 |
| 10-20 mg | Vitamin B-3 |
| 10-20 mg | Vitamin B-5 |
| 5-15 mg | Vitamin B-6 |
| 100-300 mcg | Vitamin B-9 |
| 50-200 mcg | Vitamin B-12 |
| 5-15 mg | Vitamin C |
| 1-5 mg | Zinc |
| 20-40 mg | Magnesium |
| 50-70 mg | Calcium |
| 1-4 mcg | Vitamin D |

A preferred formula of the nutritional supplement by weight follows:

|  | amount by weight |
|---|---|
| Primary Ingredients |  |
| *Calea ternifolia* powder | 500 mg |
| L-5-HTP | 20 mg |
| Vinpocetine | 2.5 mg |
| Secondary Ingredient |  |
| Melatonin | 500 mcg |
| Tertiary Ingredients |  |
| Wild Lettuce Extract 4:1 | 50 mg |
| Mugwort Extract 4:1 | 50 mg |
| DMAE | 10 mg |
| Passionflower Extract 10:1 | 22.5 mg |
| Green Tea Extract 10:1 | 10 mg |
| Additional Ingredients |  |
| Vitamin B-1 | 1.4 mg |
| Vitamin B-2 | 10 mg |
| Vitamin B-3 | 15 mg |
| Vitamin B-5 | 15 mg |
| Vitamin B-6 | 10 mg |
| Vitamin B-9 | 200 mcg |
| Vitamin B-12 | 100 mcg |
| Vitamin C | 10 mg |
| Zinc | 3 mg |
| Vitamin D | 2 mcg |
| Magnesium | 30 mg |
| Calcium | 60 mg |

When considering lucid dreaming, one of the key elements, especially at a high level, is that the dreamer not only realizes they are in a dream but that they have the potential to control the progress and outcome of the dream. The following examples are summaries of testimonials of people who took the nutritional supplement of the invention as a sleep aid and not only were able to lucidly dream but were able, through their heightened awareness and control, to change what had been recurrent patterns in their dreams and their lives.

EXAMPLES

Example 1

In this example, the individual kept having recurrent nightmares over a period of about 20 years. In the dream, the person would start across a bridge and be grabbed by a monster that would begin to crush him as he was being dragged under water. When he realized that he would soon drown, he would start screaming, waking not only himself but his bed partner, as well. This person started taking the nutritional supplement of the invention and, after several more dreams like this, gradually increased his awareness, or lucidity, to the point where he was able to confront the monster and eventually was able to exercise enough control over the outcome of the dream that he killed the monster. The nightmares stopped.

Apparently, the monster was a dream created manifestation of a real person that had abused him in the past. When the dreamer and the abuser faced each other in court to resolve a legal matter, he had gained the confidence to not be afraid of the abuser any more and won the case. In this instance, the nutritional supplement of the invention allowed him, through lucid dreaming, to conquer a long entrenched fear.

Example 2

The individual in this example had been similarly experiencing recurrent nightmares since he was about 10 years old. In the nightmare, this person was chased by a dark, faceless entity and would frequently awaken screaming. However, after beginning taking the nutritional supplement of the invention, he began dreaming more and more lucidly, to the point where he soon realized that he could control his reaction to the faceless entity. He soon was able to angrily confront the entity which allowed him to rid himself of this recurrent dream. He used his experience with the recurrent nightmare that he could exercise control, through lucidly dreaming, that he could adjust his normally negative reactions to anxiety producing events in his life into positive reactions, thus enabling him to function better in the world.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A nutritional supplement comprising:
effective amounts of primary ingredients *Calea ternifolia* powder, L-5-Hydroxytryptophan and Vinpocetine; an effective amount of a secondary ingredient melatonin; and, effective amounts of tertiary ingredients Wild Lettuce Extract 4:1, Mugwort Extract 4:1, Dimethyaminoethanol powder (DMAE), Passionflower Extract 10:1, and Green Tea Extract 10:1.

2. The nutritional supplement of claim 1 further comprising effective amounts of additional ingredients selected from the group consisting of Vitamin B-1, Vitamin B-2, Vitamin B-3, Vitamin B-5, Vitamin B-6, Vitamin B-9, Vitamin B-12, Vitamin C, and Zinc.

3. The nutritional supplement of claim 2 wherein the effective amounts of the additional ingredients are:

| | |
|---|---|
| Vitamin B-1 | 1.4 mg |
| Vitamin B-2 | 10 mg |
| Vitamin B-3 | 15 mg |
| Vitamin B-5 | 15 mg |
| Vitamin B-6 | 10 mg |
| Vitamin B-9 | 200 mcg |
| Vitamin B-12 | 100 mcg |
| Vitamin C | 10 mg, and |
| Zinc | 3 mg. |

4. The nutritional supplement of claim 1 wherein the effective amounts of the ingredients, by relative weight ratios, are:

| | |
|---|---|
| 200-250 | *Calea ternifolia* powder |
| 15-25 | Wild Lettuce Extract 4:1 |
| 15-25 | Mugwort Extract 4:1 |
| 3-5 | L-5-HTP |
| 4-6 | DMAE |
| 7-10 | Passionflower Extract 10:1 |
| 3-5 | Green Tea Extract 10:1 |
| 0.5-2 | Vinpocetine, and |
| 0.1-0.15 | Melatonin. |

5. A method of assisting a human in going to sleep comprising administering to the human, prior to going to sleep, a nutritional supplement having an effective amount of primary ingredients *Calea ternifoliai* powder, L-5-Hydroxytryptophan and Vinpocetine; an effective amount of a secondary ingredient Melatonin; and effective amounts of the tertiary ingredients Wild Lettuce Extract 4:1, Mugwort Extract 4:1, Dimethyaminoethanol powder (DMAE), Passionflower Extract 10:1, and Green Tea Extract 10:1.

6. The method of claim 5 further comprising administering effective amounts of additional ingredients selected from the group consisting of Vitamin B-1, Vitamin B-2, Vitamin B-3, Vitamin B-5, Vitamin B-6, Vitamin B-9, Vitamin B-12, Vitamin C, and Zinc.

7. The method of claim 6 wherein the effective amounts of the additional ingredients are:

| | |
|---|---|
| Vitamin B-1 | 1.4 mg |
| Vitamin B-2 | 10 mg |
| Vitamin B-3 | 15 mg |
| Vitamin B-5 | 15 mg |
| Vitamin B-6 | 10 mg |
| Vitamin B-9 | 200 mcg |
| Vitamin B-12 | 100 mcg |
| Vitamin C | 10 mg, and |
| Zinc | 3 mg. |

8. The method of claim 5, wherein the effective amounts of the ingredients, by relative weight ratios, are:

| | |
|---|---|
| 200-250 | *Calea ternifolia* powder |
| 15-25 | Wild Lettuce Extract 4:1 |
| 15-25 | Mugwort Extract 4:1 |
| 3-5 | L-5-HTP |
| 4-6 | DMAE |
| 7-10 | Passionflower Extract 10:1 |
| 3-5 | Green Tea Extract 10:1 |
| 0.5-2 | Vinpocetine, and |
| 0.1-0.15 | Melatonin. |

9. A method of enhancing lucid dreaming in a person comprising administering to the person, prior to going to sleep, a nutritional supplement having an effective amount of primary ingredients *Calea ternifoliai* powder, L-5-Hydroxytryptophan and Vinpocetine; an effective amount of a secondary ingredient Melatonin; and effective amounts of the tertiary ingredients Wild Lettuce Extract 4:1, Mugwort Extract 4:1, Dimethyaminoethanol powder (DMAE), Passionflower Extract 10:1, and Green Tea Extract 10:1.

10. The method of claim 9 further comprising administering effective amounts of additional ingredients selected from the group consisting of Vitamin B-1, Vitamin B-2, Vitamin B-3, Vitamin B-5, Vitamin B-6, Vitamin B-9, Vitamin B-12, Vitamin C, and Zinc.

11. The method of claim 10 wherein the effective amounts of the additional ingredients are:

| | |
|---|---|
| Vitamin B-1 | 1.4 mg |
| Vitamin B-2 | 10 mg |
| Vitamin B-3 | 15 mg |
| Vitamin B-5 | 15 mg |
| Vitamin B-6 | 10 mg |
| Vitamin B-9 | 200 mcg |
| Vitamin B-12 | 100 mcg |
| Vitamin C | 10 mg, and |
| Zinc | 3 mg. |

12. The method of claim 9, wherein the effective amounts of the ingredients, by relative weight ratios, are:

| | |
|---|---|
| 200-250 | *Calea ternifolia* powder |
| 15-25 | Wild Lettuce Extract 4:1 |
| 15-25 | Mugwort Extract 4:1 |
| 3-5 | L-5-HTP |
| 4-6 | DMAE |
| 7-10 | Passionflower Extract 10:1 |
| 3-5 | Green Tea Extract 10:1 |
| 0.5-2 | Vinpocetine, and |
| 0.1-0.15 | Melatonin. |

\* \* \* \* \*

UNITED STATES PATENT AND TRADEMARK OFFICE
CERTIFICATE OF CORRECTION

PATENT NO. : 8,092,840 B2  Page 1 of 1
APPLICATION NO. : 11/927836
DATED : January 10, 2012
INVENTOR(S) : Luciano It is certified that error appears in the above-identified patent and that said Letters Patent is hereby corrected as shown below:

Claim 5 (Column 6, line 15): replace "*Calea ternifoliai*" with "*Calea ternifolia*"

Claim 9 (Column 6, line 57): "*Calea ternifoliai*" should read "*Calea ternifolia*"

Signed and Sealed this
Thirteenth Day of March, 2012

David J. Kappos
*Director of the United States Patent and Trademark Office*